United States Patent [19]

Boussert

[11] 4,350,616

[45] Sep. 21, 1982

[54] METHOD OF MAKING CATALYSTS FOR THE PRODUCTION OF ETHYLENE OXIDE

[75] Inventor: Anne S. Boussert, Baton Rouge, La.

[73] Assignee: The Dow Chemical Company, Midland, Mich.

[21] Appl. No.: 165,512

[22] Filed: Jul. 3, 1980

[51] Int. Cl.$^3$ .................. B01J 21/04; B01J 23/02; B01J 23/04; B01J 23/66

[52] U.S. Cl. .................................. 252/463; 252/476

[58] Field of Search .......................... 252/463, 476; 260/348.34

[56] References Cited

U.S. PATENT DOCUMENTS

| | | | |
|---|---|---|---|
| 3,575,888 | 4/1971 | Long | 252/476 |
| 3,887,491 | 6/1975 | Ramirez et al. | 252/476 X |
| 4,033,903 | 7/1977 | Maxwell | 252/476 |
| 4,066,575 | 1/1978 | Winnick | 252/476 X |
| 4,177,169 | 12/1979 | Rebsdat et al. | 252/476 |

FOREIGN PATENT DOCUMENTS 2002252 2/1979 United Kingdom ................ 252/475

*Primary Examiner*—W. J. Shine
*Attorney, Agent, or Firm*—A. Cooper Ancona

[57] ABSTRACT

An improved process for obtaining a silver catalyst promoted with cesium wherein said silver crystals average about 0.4$\mu$ in diameter and wherein 75–86% of the crystals are within the range of 0.2 to 0.6 $\mu$ in diameter. This catalyst is prepared without any special heat treatment after the initial reduction of the silver salt and prior to incorporating the cesium promoter.

9 Claims, No Drawings

METHOD OF MAKING CATALYSTS FOR THE PRODUCTION OF ETHYLENE OXIDE

BACKGROUND OF THE INVENTION

This invention relates to a novel method of preparing a silver catalyst and its use in the process of making ethylene oxide by the partial oxidation of ethylene in the vapor phase. Silver-containing catalysts in which the catalytically active component is the metal itself are well known in the art. An important use for the catalyst is in the direct oxidation conversion of alkenes to the corresponding vicinal epoxides, particularly in preparing ethylene oxide from ethylene by reacting ethylene with oxygen in the vapor phase.

Methods known to the art for making such catalysts include soaking a carrier or support in aqueous solutions of silver salts to impregnate it. Thereafter the thus-impregnated salts are reduced to silver metal prior to utilization in the process for oxidizing ethylene. Reduction is normally accomplished by heating in the presence of a reducing agent or by thermal decomposition of the salt. This is done at temperatures within the range of 125° C. to 400° C. and preferably from 200° C. to 300° C. Alternatively, the silver salt may be deposited from a slurry. Either slurry or solution also may contain a reducing agent, or the reducing agent may be subsequently applied.

The commonly used reducing agents are organic compounds which include polyhydric alcohols, such as liquid glycols (e.g. ethylene, propylene, and butylene glycols), glycerol, aqueous sugar solutions, aqueous polyvinyl alcohol solutions, the polyglycols, (e.g. polyethylene and polypropylene glycols) preferably of relatively low molecular weight; also included are aqueous solutions of such polyglycols, the water soluble glycol alkyl ethers, and the like. Other excellent reducing agents are high-boiling esters of carboxylic acids such as dioctyl sebacate, dibutyl phthalate, and the like.

One of the criteria for commercially useful silver catalysts is that the silver be finely divided and relatively homogeneously dispersed on the catalyst support. Dispersing agents are advantageously used in order to obtain such silver deposits, especially suitable as dispersing agents are organic amines such as ethylene diamine and ethanolamine and others disclosed in U.S. Pat. No. 3,702,259; and those naturally occurring gums such as disclosed in U.S. Pat. No. 3,887,491. These natural gums are, for example, karaya, ghatti, and tragacanth, which are plant exudates; root or seed extracts, such as guar, saponin and locust bean, psyllium seed, and quince seed. Seaweed extracts such as agar, carrageenin and furcellaran are also useful as well as others such as gelatin, casein, and pectin. Certain chemically modified derivatives of starch or cellulose and poly sacharides (the unmodified forms are which are insoluble) are also included as substances classifiable as gums and are useful as dispersing agents in the preparation of catalysts.

The condition of silver, that is the state of subdivision, is of great importance in the successful, efficient utilization of these catalysts for ethylene oxidation to ethylene oxide. This is recognized in U.S. Pat. No. 3,043,854 wherein a process for making catalysts having silver particles of less than $1\mu$ is described. The importance of uniformity of size is also recognized in U.S. Pat. No. 3,702,259 wherein small, uniform-sized particles are produced by the use of a solubilizing-reducing agent such as, for example, ethylene diamine or ethanolamine or their mixtures.

Supports known to be useful for making silver catalysts are for example alumina, zirconia, corundum, mullite, silicon carbide and carbon. Alumina is preferred and especially a porous alumina of low surface area, i.e. less than one square meter per gram.

While silver is the metal most useful from a commercial standpoint in providing the catalytic effect necessary to obtain ethylene oxide, most commercial catalysts additionally contain small amounts of a promoter. The amount employed is usually from a few parts per million up to one or two percent, based on the weight of the total catalyst. Representative promoters include the alkali and alkaline earth metals which are usually present as their oxides. Thus lithium, sodium, potassium, rubidium, cesium, calcium, barium, cadmium, and the like, are added as their salts to the solution of the silver salt which is applied to the support and on subsequent heating are converted to their oxides.

Other ways known to the art of adding the promoter compound are to add it to the support prior to (see U.S. Pat. No. 3,563,914) or subsequent to (see U.S. Pat. Nos. 2,142,948 and 2,404,438) the application of the silver salt. In each case the particular salt applied is dried prior to applying the solution of the second salt. In a more recent patent (U.S. Pat. No. 4,168,247), the promoters are applied after reduction of the salt to the silver metal coating, but then the entire catalyst is heat treated. To insure adequate penetration of the pores of the support, a vacuum is applied when applying the aqueous solutions of the silver salt or of the promoter salt. This is described in U.S. Pat. No. 3,575,888. Generally the promoters are converted to their oxides and the silver salt is reduced to silver.

A heat treatment of the catalyst prior to applying cesium as a promoter is taught in U.S. Pat. No. 4,033,903. This heat treatment is in addition to the heating employed to (1) reduce the silver compound on the support to silver metal and (2) remove any reducing agent remaining on the catalyst. According to this patent one can heat-treat a new catalyst before applying the cesium, or apply cesium to one which has been employed as a catalyst in a reactor for the production of ethylene oxide, i.e., heat-treated by use. It is taught that such heat-treatment produces optimum stabilized particles having average diameters between 0.2 and $4\mu$ and especially of between 0.4 and $2.5\mu$.

It has now been discovered that the silver catalysts prepared by the methods disclosed in U.S. Pat. No. 3,887,491 and in copending application U.S. Ser. No. 043,414 produce a catalyst having a predominance of silver particles within the range of optimum stabilized particles taught in U.S. Pat. No. 4,033,903. While the range taught in this patent is from 0.2 to $4\mu$, most of the particles produced by the methods of U.S. Pat. No. 3,887,491 and the above copending application are equal to or less than $1\mu$, predominantly in the range of from 0.2 to $0.6\mu$ in diameter. Such silver particles are especially suitable for the application of cesium as a promoter. It is not required that the silver catalyst be heat-treated to obtain the desired particle size for the silver prior to the application of the cesium as taught in U.S. Pat. No. 4,033,903 or thereafter as in U.S. Pat. No. 4,168,247, both noted above.

SUMMARY OF THE INVENTION

The present invention is an improved process for preparing silver catalysts useful in production of ethylene oxide which comprises impregnating a catalyst support with an aqueous solution of a silver compound so as to assure penetration of substantially all of the pores of the support; drying the thus impregnated support; impregnating the dried support with a reducing agent to assure penetration of substantially all of the pores of the support. Following this the so-impregnated support is heated at a temperature and for a period of time sufficient to accomplish the reduction of the silver compound to silver metal and to remove excess reducing agent to provide a catalyst having silver particles, 87-95% of which are of a diameter within the range of 0.2 to 1.0μ. The silver-containing catalyst is then impregnated with cesium by treating said catalyst with an alcoholic solution of a cesium compound after which the alcohol solvent is removed leaving the cesium compound on the support.

DETAILED DESCRIPTION OF THE INVENTION

In a representative operation an aqueous solution containing 54.8% silver nitrate, and 0.38% barium nitrate was used to impregnate a catalyst support consisting of 3/16" diameter spherical porous alumina pellets having a surface area less than 1 m$^2$/g. The amount of solution used was an amount sufficient to completely wet the catalyst without any appreciable excess of solution. A vacuum was then applied at ambient temperature for 30 minutes and drying was accomplished by heating to a temperature of 100° C. while maintaining that vacuum. The dry impregnated support, while still under vacuum, was then contacted with a high-boiling ester as a reducing agent, in this case dioctyl sebacate, which was heated to a temperature of about 100° C. to allow penetration of all the pores by the reducing agent. Other high boiling esters suitable as reducing agents include diethyl phthalate, dibutyl phthalate, diethyl sebacate, dibutyl sebacate, dicapryl sebacate, dibutyl azelate, dioctyl azelate and dicapryl azelate. When all of the reducing agent had been absorbed, the support was then placed into a kiln heated to a temperature of 400° C. for a sufficient time to reduce the silver salt and remove excess reducing agent. The silver and barium on the support were determined to be about 10% and 180 ppm, respectively. The entire process was then repeated in order to obtain a catalyst containing a greater amount of silver. After the second processing the catalyst contained 17.9% silver and 360 ppm barium.

Alternatively the reducing agent is dissolved in a carrier, e.g. mineral oil, and the catalyst support containing the silver and barium salts is immersed therein and a vacuum applied to obtain penetration of the pores by the reducing agent. Also the mineral oil itself may be employed as the reducing agent. Thereafter the catalyst support is removed, drained of excess liquid and heated to 400° C. as before to reduce the silver salt to silver and the promoter salt to an oxide.

The solutions from which the catalytic salts are applied are aqueous solutions containing generally from 15% up to 65% by weight of silver nitrate and from 0.01 to 0.7% by weight of the barium nitrate. The dispersing agent, preferably the naturally occurring gums, is used in an amount of from about 0.05% to 15.0% by weight of the solution. The solution is of sufficient concentration to provide from 12 to 23% silver on the finished catalyst and from 100 to 1,000 parts per million of barium. The temperature of drying the support after application of the silver and promoter salts is from about 50° C. to about 150° C., preferably from about 75° C. to about 125° C. Since the high-boiling esters (i.e. having boiling points above 300° C.) are very viscous at room temperature, heat and vacuum should preferably be applied in order to penetrate the small pores of the catalyst support so as to allow complete reduction of all of the silver salts on the support. This is true even though the reducing agent is applied in a carrier liquid. Heat is applied to obtain a temperature in the same range as for the preceding drying step, i.e. 50° C.-150° C. The vacuum, when employed for the impregnation of the silver salt, the drying step and the application of the reducing agent, is essentially the same and within the range of 20" to 30" Hg. The reduction itself and removal of excess reducing agent is conducted at temperatures within the range of 150° C. to 400° C., but preferably at from 180° C. to 300° C.

The resulting silver catalyst is then treated with a solution of a cesium salt, e.g., Cs$_2$CO$_3$, in a lower alkanol, e.g., methanol, to apply a cesium promoter to the silver. Sufficient of the cesium salt is employed in the solution to provide the finished catalyst with a Cs content of from about 50 to 350 ppm based on the total weight of catalyst support. This solution may be applied under vacuum to obtain a more uniform coating of the promoter, both on the surface and in the pores of the support. The solvent methanol is then evaporated, preferably under vacuum, at a temperature of from about ambient to 150° C. Other cesium salts useful in the application are CsOH, CsNO$_3$, CsCl and CsClO$_4$. The resulting catalyst contains from about 50 to 350 ppm. Cs.

The following table shows representative silver particle sizes of catalysts prepared according to the methods disclosed in U.S. Pat. No. 3,887,491 and the above identified copending application.

| Particle size (μ) | '491 (%) | Appln. (%) |
| --- | --- | --- |
| <0.2 | 9.3 | 2.9 |
| 0.2-0.6 | 77.7 | 85.7 |
| 0.7-1.0 | 10.0 | 9.3 |
| >1.0 | 3.0 | 2.1 |

EXAMPLE IA (Comparative)

One hundred grams of 3/16" diameter spheres of low purity alumina support were dried at 70° C. under 30" vacuum for 30 minutes. The support was vacuum impregnated with 28.5 g of a solution containing 65% silver nitrate in demineralized water and 20 g of 30% gum arabic in demineralized water. The impregnated support was vacuum dried at 70° C. for 30 minutes in a flask with rotation and then 20 ml of dioctyl sebacate (DOS) was vacuum impregnated onto the silver containing support. The impregnated support was heated at 300° C. for 45 minutes to reduce the silver and remove excess DOS. The impregnation with silver nitrate, drying, impregnation with DOS, and reduction step were repeated. This catalyst, containing 19% Ag by weight, was evaluated by placing seven grams of catalyst in a lab reactor. A feed mixture containing 6% ethylene, 6.5% oxygen, 7% carbon dioxide, 200 ppb ethylene dichloride, and 80.5% nitrogen, (volume percent) at 50 psig was passed at a rate of 0.3 SCFH over the catalyst.

The yield to EO at 25% ethylene conversion was 71.5% at 234° C.

EXAMPLE IB

Twenty-five grams of a catalyst prepared according to the procedure of Example IA were placed in a flask containing 0.766 g of 1% $Cs_2CO_3$ in 30 ml of methanol. The flask was rotated under vacuum at 70° C. until all the methanol had evaporated. The resulting catalyst was dried at 110° C. for 2 hours. It contained 250 ppm Cs. It was evaluated as in Example 1A above using the same feed and flow rate. The yield to EO at 25% conversion was 72.7% at 247° C.

In like manner catalysts were prepared in which barium was included (as $Ba(NO_3)_2$) with the silver nitrate as a promoter, and compared with and without cesium.

EXAMPLE II

The catalysts in this experiment were prepared in larger batches for pilot scale runs using 5/16" diameter spheres of the same low purity alumina used in Example IA and the carrier was impregnated in the same manner as in Examples IA and IB. Amounts of silver, barium and cesium along with results of the use of each catalyst in ethylene oxide manufacture are shown in the following table. Feed Conditions were: 900 SCFH (standard cu. ft./hr.), 250 psig, 6 mol % $C_2H_4$, 6.2 mol % $O_2$, 7.5 mol % $CO_2$, Balance $N_2$.

|   | Catalyst Components | | | Ave. | | |
|---|---|---|---|---|---|---|
|   | Ag Wt. % | Ba ppm | Cs ppm | Temp. (°C.) | Conv. (%) | Yield (%) |
| A | 20.0 | — | — | 249 | 25.8 | 69.2 |
| B | 20.0 | — | 313 | 260 | " | 74.0 |
| C | 19.6 | 930 | — | 252 | " | 71.0 |
| D | 20.0 | 845 | 286 | 256 | " | 73.5 |

EXAMPLE IIIA (Comparative)

In the manner of Example IA, 40 g. of the same low purity support was treated in the same way except that the reduction was carried out in mineral oil instead of employing DOS. The reduction was conducted at 250° C. for 30 minutes, followed by the removal of excess mineral oil by heating at 300° C. for 45 minutes. The above procedure was repeated to obtain a catalyst containing 19% silver. This catalyst was employed to make ethylene oxide by using the same feed mixture employed in Example IA. The yield to EO at 25% conversion at a temperature of 245° was 75%. This yield was 1.7% points better than a standard catalyst run simultaneously at the same conversion.

EXAMPLE IIIB

Twenty-five grams of a catalyst prepared according to the procedure of Example IIIA were placed in a flask containing 0.919 g of 1% $Cs_2CO_3$ in 30 ml of methanol. The flask was rotated under vacuum at 70° C. until all the methanol had evaporated. Catalyst contained 300 ppm Cs. The catalyst was heated at 100° C. for 2 hours. The catalyst was evaluated in the same manner as Example IA. The yield to EO at 25% ethylene conversion was 78.0% at 239° C. This yield was 5.5% points better than standard. Thus the cesium-treated catalyst provided 3.8% improvement in yield over the untreated catalyst.

EXAMPLE IV

A single reactor (in the secondary stage) in a plant process employing four reaction stages had been run for more than one year containing a catalyst prepared by burdening 5/16" low purity alumina spheres with aqueous silver nitrate and barium nitrate as in Example II above by impregnating and drying under vacuum and reducing the silver nitrate to silver in a mineral oil bath containing DOS as described in U.S. Pat. No. 3,887,491. Excess mineral oil and reducing agent were removed by heating as described herein above. The process was repeated to obtain a catalyst containing about 19.5% Ag and 0.26% Ba by weight.

The same reactor was then run for a similar period of time under substantially the same conditions, i.e. to obtain the same conversion of ethylene, using a catalyst which had been prepared in substantially the same manner, but subsequently treated with cesium hydroxide in methanol to provide a catalyst which contained about 20.0% Ag, 0.26% Ba and 260 ppm Cs.

The cesium treated catalyst gave a yield of about 70% during the 1st month of operation while the untreated catalyst gave a yield of 66%, both run at the same conversion. By the 12th month the cesium treated catalyst was producing a yield of slightly more than 65%, while the untreated catalyst produced a yield of about 64%. Thus, the cesium treated catalyst performs better even after extended use in the plant than the untreated silver catalyst. This approximately 1% yield difference is a significant one when considering the large amount of product made.

I claim:

1. In a process for making an improved silver catalyst for use in producing ethylene oxide, wherein ethylene and oxygen are reacted in the vapor phase at an elevated temperature in the presence of said catalyst, by
    (a) impregnating a porous alumina support by contacting said support with an aqueous solution of a silver salt,
    (b) drying said impregnated support
    (c) impregnating said dry support with a reducing agent selected from high boiling organic esters, mineral oil or mixtures thereof by contacting said support with said reducing agent,
    (d) heating said support to reduce said silver salt on said support to silver metal and to remove residual reducing agent, the silver metal made thereby characterized in having a predominance of particles of no more than about one micron in diameter,
the improvement which consists of:
    (1) impregnating said silver-containing support with cesium by contacting said silver-containing support with a solution of cesium compound in a lower alkanol, and
    (2) heating said cesium-impregnated silver-containing support at a temperature sufficient to remove said lower alkanol.

2. The process of claim 1 wherein a soluble alkaline earth metal salt is included as a promoter in the aqueous solution of the silver salt.

3. The process of claim 2 wherein the alkaline earth metal salt is a barium salt.

4. The process of claim 3 wherein the barium salt is barium nitrate.

5. The process of claim 4 wherein the silver salt is silver nitrate.

6. The process of claim 2 wherein the lower alkanol is methanol.

7. The process of claims 2 or 3 wherein the organic ester is selected from the group of esters consisting of diethyl phthalate, dibutyl phthalate, diethyl sebacate, dibutyl sebacate, dioctyl sebacate, dicapryl sebacate, dibutyl azelate, dioctyl azelate and dicapryl azelate.

8. The process of claim 1 wherein steps a, b, c, d and l are accomplished under vacuum.

9. The process of claims 1, 2 or 3 wherein the reducing agent is mineral oil.

* * * * *

UNITED STATES PATENT AND TRADEMARK OFFICE
CERTIFICATE OF CORRECTION

PATENT NO. : 4,350,616

DATED : September 21, 1982

INVENTOR(S) : Anne S. Boussert

It is certified that error appears in the above—identified patent and that said Letters Patent is hereby corrected as shown below:

Col. 5, line 64, change "100°" to --110°--.

Col. 7, line 5, Claim 7, insert the figure --1-- after the word claims.

Signed and Sealed this

Twenty-second Day of February 1983

[SEAL]

Attest:

Attesting Officer

GERALD J. MOSSINGHOFF

Commissioner of Patents and Trademarks